United States Patent
Zaloom et al.

(10) Patent No.: US 6,664,019 B2
(45) Date of Patent: Dec. 16, 2003

(54) ALUMINUM PRINTING PLATES AND METHOD OF MAKING

(75) Inventors: Jeffrey G. Zaloom, Waukesha, WI (US); Bruce Holman, III, Milwaukee, WI (US); Zhengzhe Song, Waukegan, IL (US); David C. Tanck, Oak Creek, WI (US)

(73) Assignee: Printing Developments Inc., Racine, WI (US)

( * ) Notice: Subject to any disclaimer, the term of this patent is extended or adjusted under 35 U.S.C. 154(b) by 44 days.

(21) Appl. No.: 09/902,416

(22) Filed: Jul. 10, 2001

(65) Prior Publication Data

US 2001/0046645 A1 Nov. 29, 2001

Related U.S. Application Data

(60) Continuation-in-part of application No. 09/525,262, filed on Mar. 14, 2000, now abandoned, which is a division of application No. 08/666,169, filed on Jun. 19, 1996, now Pat. No. 6,037,085.

(51) Int. Cl.$^7$ .............................. G03F 7/012; G03F 7/30
(52) U.S. Cl. .................... 430/167; 430/278.1; 430/302; 205/213; 205/214; 148/285; 148/703
(58) Field of Search .................. 148/285, 703; 205/213, 214; 430/167, 302, 278.1

(56) References Cited

U.S. PATENT DOCUMENTS

| | | | |
|---|---|---|---|
| 4,116,695 A | | 9/1978 | Mori et al. ..................... 96/86 |
| 4,121,980 A | | 10/1978 | Gohausen et al. ......... 204/35 N |
| 4,175,964 A | * | 11/1979 | Uchida et al. ............... 430/253 |
| 4,399,021 A | | 8/1983 | Gillich et al. .................. 204/38 |
| 4,492,616 A | | 1/1985 | Pliefke et al. ................. 204/33 |
| 4,672,022 A | * | 6/1987 | Reiss et al. ............... 430/278.1 |
| 4,714,528 A | | 12/1987 | Takeuchi et al. ............... 204/33 |
| 4,902,389 A | | 2/1990 | Nishino et al. ........... 204/129.1 |
| 5,637,441 A | | 6/1997 | Brenk et al. ............. 430/278.1 |
| 5,645,972 A | * | 7/1997 | Jonkheere .................... 430/231 |
| 5,773,194 A | * | 6/1998 | Hattori et al. ............ 430/284.1 |
| 5,811,215 A | * | 9/1998 | Van Damme et al. ....... 430/201 |
| 5,962,192 A | * | 10/1999 | Holman et al. .............. 430/302 |
| 6,037,085 A | | 3/2000 | Holman, III et al. ......... 430/18 |

FOREIGN PATENT DOCUMENTS

GB 1230447 5/1971

* cited by examiner

*Primary Examiner*—John S. Chu
(74) *Attorney, Agent, or Firm*—Arthur J. Plantamura

(57) ABSTRACT

A method of making improved aluminum printing plates comprising graining the aluminum plates, de-smutting them by treating them with nitric acid solution, then rinsing with hot water, acetating the aluminum plates, and silicating the aluminum plates. The plates are then coated with a photoresist, pattern exposed and developed. The printing plates of the invention have improved characteristics; they have excellent adhesion of the resist in image areas, and ink repellency in non-image areas. The developed printing plates have excellent durability without baking.

10 Claims, No Drawings

ALUMINUM PRINTING PLATES AND METHOD OF MAKING

This invention is a continuation-in-part of application Ser. No. 09/525,262 filed Mar. 14, 2000, now abandoned, which is a divisional of application Ser. No. 08/666,169 filed Jun. 19, 1996, now U.S. Pat. No. 6,037,085 issued Mar. 14, 2000.

This invention relates to improved aluminum printing plates that can be exposed using an infrared light source. More particularly, this invention relates to improved aluminum printing plates and to methods of preparing printing plates that are to be infrared light exposed using a positive photopolymer resist.

BACKGROUND OF THE INVENTION

Lithographic printing plates are required to be able to be exposed and imaged efficiently with high resolution; they must be capable of printing uniformly onto various substrates to produce high quality images; and they must be capable of running hundreds of thousands of copies, all at low cost. Generally, printing plates are made from lithographic grade aluminum. The plates are treated to clean their surfaces; to grain or roughen the surface to improve the adhesion of a photopolymer coating; to anodize the grained surface to improve their durability; and to treat the surface to obtain a hydrophilic surface.

Typically, the initial step in the preparation of aluminum printing plates is to clean or etch the raw aluminum, usually with an alkaline etch, which can be followed with an acid etch. The aluminum plate is then grained to promote adhesion of subsequently applied layers, and to improve the ink-water balance on a printing press. Graining is suitably done using an electrochemical method, or a combination of mechanical and electrochemical methods, to provide a uniformly roughened surface having a topography on the order of up to one micron.

The grained aluminum is usually oxidized, or anodized, forming an aluminum oxide coating, such as by treating with phosphoric or sulfuric acids using an electrochemical process. The oxidized surface is then passivated, as with a silicate coating and/or a polyvinyl phosphoric acid coating, to inhibit aluminum corrosion. This step produces a smooth coating that is durable and has a low porosity.

An image forming layer, such as a photoresist, is applied over the treated aluminum plate. For laser thermal imaging, which can be computer controlled, the plate must be able to withstand deposition of the photoresist, imaging and development of the photoresist, without adhesion loss of the photoresist to the substrate. The printing plate is then baked to "set" the resist.

In addition, the photoresist must have a wide development latitude, that is, the development of the photoresist after exposure, must be as long as possible to provide as much of a difference as possible between exposed and unexposed areas of the resist. A wide development latitude results in the possibility of using an increased photospeed, so that the resist can be exposed rapidly, increasing its reliability and providing flexibility for the choice of materials and exposure to the end user.

U.S. Pat. No. 5,962,192, based on Ser. No. 08/666,169 and issued on Mar. 14, 2000, discloses particular positive photoresists. Although they are excellent for use on copper clad metal printing plates, they did not work as well with the above conventional aluminum printing plates. Complete removal of the photoresist was not achieved, and the development latitude or range was narrow.

Thus it is an object of the present invention to prepare aluminum printing plates that can be used with the above photoresists to prepare highly durable printing plates having developed photoresists that adhere well to the plate, that have a wide development latitude for long development time, that have a clear image and that can be used to make many hundreds of thousands of copies from a single printing plate.

SUMMARY OF THE INVENTION

The present method for preparing aluminum printing plates includes the following steps in sequence:

a) treating the plate to clean its surface;

b) chemically graining the aluminum to promote good adhesion of an overlying photoresist;

c) treating with nitric acid to remove smut on the surface;

d) spraying the plate with water at a temperature of 160–180° F.;

e) treating the plate with an acetate-phosphate solution; and f) treating the plate with a silicate solution prior to applying a photoresist layer.

The photoresists are used with computer controlled laser diodes to produce a printing plate having a wide development latitude.

DETAILED DESCRIPTION OF THE INVENTION

After cleaning an aluminum printing plate, it must be treated to obtain a durable plate having a maximum development latitude, in addition to treatments that will provide good adhesion between the photoresist and the plate. The demarcation between exposed and non-exposed areas of the resist must be clear and sharp, the plate must be able to withstand numerous printing cycles, and the non-image areas of the plate must exhibit good ink repellency.

A commercially available lithographic grade aluminum printing plate about 0.008–0.020 inch thick, in accordance with the invention, is treated as follows.

a) the plate is cleaned to remove grease and dirt by immersing for about 30–45 seconds in an aqueous solution of sodium hydroxide (26–28 grams/liter) and about 3.7 grams/liter of sodium gluconate heated to a temperature of about 140° F. The aluminum plate is then rinsed with de-ionized (hereinafter DI) water.

b) the cleaned aluminum is grained by immersing in a solution of ammonium bifluoride and ammonium nitrate for about 45 seconds, and heated to about 130° F. The ammonium bifluoride is suitably employed at a concentration of about 50 to 125 grams/liter, preferably about 75 grams/liter, and the ammonium nitrate is used in a concentration of from about 1–10% of the ammonium bifluoride concentration, preferably about 10%. Nitric acid may be substituted for the ammonium nitrate. The aluminum plate is again rinsed in DI water.

c) once grained, the aluminum is sprayed with a 5–30% by volume solution of 42 Baume° nitric acid to de-smut the surface.

d) the plates are then sprayed with hot water (160–180° F.) to begin the formation of an oxide layer.

e) immediately after step d), the plates are immersed in a solution including about 10–12 grams/liter of sodium acetate, about 1 gram/liter of sodium carbonate and sufficient trisodium phosphate to bring the pH of the solution within a range of from about 10.5–11.5. After heating the solution to about 160–200° F., the plates are immersed in the solution for about 30–60 seconds. This completes the formation of the oxide layer. The aluminum plates are again rinsed with DI water.

f) the oxidized aluminum plate is then silicated by immersing for about 30–45 seconds in a solution containing about 15–25 ml/liter of a silicate solution commercially available from PQ Corporation under their tradename STAR$^{TN}$. The solution was heated to about 150–180° F. The plate was again rinsed with DI water.

Thus the present method omits a separate anodization step. However, the hot water rinse and acetate steps ensures that the resist will adhere to the metal printing plate, and permits the aluminum metal plate to behave in the same way as a prior art bi-metal plate of copper clad metal. Thus the anodization step and process baking steps can be omitted when using the present hot water rinse/acetate treatment. Because of the improved adhesion of the resist to the printing plate, the post-baking step can also be omitted. Thus the present method reduces the number of steps required to prepare a high quality printing plate having excellent adhesion, wide development latitude and great durability.

A positive photopolymer, such as described in U.S. Pat. No. 5,962,192, is then applied to the treated aluminum surface by spin coating. These positive photopolymers are made from an organoazide compound mixed with a suitable polymeric resin and one or more dyes that are sensitive to light emitted by the particular laser used for exposure. Additional ingredients, such as a pigment that improves the contrast between the resist layer and an underlying substrate, and surfactants, designed to adjust the texture of the resist so that it will form a smooth coating and will have a uniform thickness on the prepared aluminum plate, can also be added. Typically, lithographic resists of the present type have a dry thickness of about 40–80 microinches. The resist is mixed with a suitable organic solvent so that it can be applied to the printing plates as a thin film having a uniform thickness. The solids are generally present at a concentration of about 3–5% by weight in the organic solvent.

Polymeric resins suitable for use in the photoresist include polyvinyl formal resin and its derivatives, polymers and copolymers of acrylates and methacrylates, styrene and the like.

Suitable organoazide compounds can be mono- or multi-functional and generally have more than one azide group. The azides are used together with suitable dyes, such as infrared absorbing dyes, that are photosensitive to the light emitted by the particular laser used for patterning the resist. It is believed that high intensity laser light excites electrons in the dye absorbers so that the laser light is transformed into heat energy. The heat energy is transmitted to the organoazide compound, dissociating the azide, and making it soluble in a developer solvent. The dye chosen for the present resists must be sensitive to the frequency of the laser used to expose the resist, and must be able to absorb the radiation from the laser and convert it to heat. Various dyes are available commercially that are sensitive to infrared light having various emission frequency ranges for use with laser diodes, infrared lasers, YAG lasers, carbon dioxide lasers and the like. What is important is that the dye be sensitive in the same region of the spectrum as the light emitted by the light source used to pattern the resist.

Flood exposure by ultraviolet light can be used to improve the insolubility of the insoluble portions of the resist after exposure to the patterning light. The organoazides remaining on the substrate will cross link in the presence of ultraviolet light, making them less permeable to the developer solvent. This can suitably be done prior to laser exposure.

The resist is then developed using conventional developer solutions and equipment. The developer solubilizes the exposed regions of the resist, and rinses it away. The presence of a pigment is advantageous because one can determine visually when the resist has been removed down to the substrate in the image exposed regions.

The resultant aluminum printing plates will carry printing inks, which can be transferred to another medium, such as paper.

The invention will be further described in the following example, but the invention is not meant to be limited to the details described therein.

In the Example, adhesion of the resist was determined by soaking the plate in FS-70 fountain solution (Printing Developments, Inc) for three days. A clear adhesive tape was applied to the plate and the tape peeled away. Adhesion is deemed to be "good" if no resist is removed with the tape, specifically in the fine screen areas.

Development latitude was determined by the range of development time required to produce a clean metal surface in the non-image areas, without degradation of the resist in the image areas. The printing plates were then used to reproduce the pattern from the printing plate onto another surface, such as paper.

EXAMPLE

Part One

Printing plates were prepared by graining, acid de-smutting, hot water rinsing, acetating and silicating in sequence as described hereinabove.

Part Two

A photopolymer solution was made by mixing 2.34 grams of bis 2,6-(4-azidobenzylidene)-4-methylcyclohexanone, 0.9 gram of an infrared absorbing dye available as Projet 825 from Avecia, 0.9 gram of methyl red, 0.1 gram of a fluorocarbon surfactant available as FC 431 from 3M Company, 15.4 grams of a polyvinyl formal available as Vinylec H from Cisso Corporation, 400 grams of chlorobenzene and 100 grams of butanol.

After spinning the aluminum printing plates as described hereinabove in a spin coater for 60 seconds, the coated plates were dried for two minutes at 235° F. The plates were exposed to ultraviolet light from a high pressure mercury vapor lamp that emits 450 mJ/cm$^2$.

The plates were then image exposed using a computer controlled 830 nm laser diode (150 mJ/cm$^2$) in a plate setter. The plates were then developed with a developer solution, 195D, available from Printing Developments Inc.

The ink repellency of the non-image areas was very good. Little water was required on press; thus the proper ink-water balance was easy to maintain. Coated plates demonstrated a durability of 500,000 to 800,000 impressions without either pre-baking or post-baking the plates.

Control 1

Printing plates were prepared using a hot water rinse, acetating and silicating of aluminum plates, but omitting the graining and de-smutting steps. The adhesion of the resist was very poor, and it could be removed by rubbing with a wet cloth. The ink repellency of the non-image area was good.

Control 2

Printing plates were prepared by graining, de-smutting, hot water rinsing and silicating but omitting the acetating step. Adhesion of the resist was poor, but the ink repellency of the non-image area was good.

Control 3

Printing plates were prepared by graining, acetating and silicating, but omitting the acid de-smutting and hot water rinse steps. The overall adhesion was good, but there were random parts of the plate where resist adhesion was very poor. Thus adhesion was non-uniform. Ink repellency of the non-image area was good.

Control 4

Printing plates were prepared by graining, acid de-smutting, hot water rinsing and acetating, but omitting the silicating step. The resist adhesion was excellent, but the ink repellency of the non-image area was very poor.

Thus it is apparent that all of the steps employed in the Example are required to produce an improved printing plate. Graining is required to produce sufficient adhesion of the resist to the substrate; treatment with acid follows for a de-smutting step; a hot water rinse is required to start oxidation of the plates without a separate anodization step. Acetating to complete the oxidation of the aluminum surface and silicating are required to impart sufficient adhesion and ink repellency to a grained plate. However, a separate anodization step of the grained aluminum surface, and baking steps during the plate processing are not required.

The printing plates of the invention have several additional advantages, in addition to a wider development latitude. They are also hydrophilic without saturating the plate with water; they run drier and come up to color faster than prior art plates. Thus less paper, about 1–2%, less ink, typically 1–5% less, and less time are required to begin to run good copies. Further, more copies can be made from each printing plate. Because the plate runs drier, paper copies do not become wetted, web breaks are fewer and quality is higher. Most importantly, the printing plates of the invention do not require any baking to achieve run lengths of 500,000 to 800,000 impressions.

Although the invention has been described in terms of specific embodiments and ingredients, one skilled in the art will know that other ingredients can be substituted, including the photoresist. Thus the invention is only to be limited by the scope of the appended claims.

We claim:

1. A method of preparing aluminum printing plates comprising the following steps in sequence:
   a) graining the aluminum;
   b) de-smutting the aluminum;
   c) rinsing with hot water;
   d) acetating the aluminum; and
   e) silicating the aluminum.

2. A method according to claim 1 wherein a layer of a cross linkable azide photoresist solution is spun onto the plates after the silicating step.

3. A method according to claim 2 wherein the photoresist is flood exposed with ultraviolet light.

4. A method according to claim 2 wherein the photoresist is pattern exposed with a light source and developed to dissolve soluble portions of the photoresist.

5. A method according to claim 4 wherein the photoresist is exposed using a computer controlled laser diode.

6. A grained aluminum printing plate prepared according to the method of claim 1 having a layer of oxide having a maximum thickness of about 0.5 micron.

7. A grained aluminum printing plate according to claim 6 wherein the oxide layer is from 0.1 to 0.3 micron thick.

8. A grained aluminum printing plate according to claim 6 having a layer of silicate over the oxide layer.

9. A grained aluminum printing plate prepared according to the method of claim 1 having a layer of oxide having a maximum thickness of 0.5 micron, a layer of silicate thereover and a layer of a cross linkable azide photoresist thereover.

10. A printing plate according to claim 9 wherein said photoresist has been pattern exposed with light and developed with a developer solvent.

* * * * *